United States Patent [19]

Knohl et al.

[11] B 3,997,659

[45] Dec. 14, 1976

[54] HAIR BLEACHING COMPOSITIONS CONTAINING AN ARGININE COMPOUND

[75] Inventors: Richard B. Knohl; Eugene Zeffren, both of Wyoming, Ohio

[73] Assignee: The Procter & Gamble Company, Cincinnati, Ohio

[22] Filed: Apr. 26, 1974

[21] Appl. No.: 464,593

[44] Published under the second Trial Voluntary Protest Program on March 9, 1976 as document No. B 464,593.

Related U.S. Application Data

[63] Continuation of Ser. No. 129,554, March 30, 1971, abandoned.

[52] U.S. Cl. .................................. 424/62; 8/111; 252/186; 424/DIG. 3; 424/70; 424/359; 424/362
[51] Int. Cl.² ............................... A61K 7/135
[58] Field of Search ............... 424/DIG. 3, 62, 319, 424/359; 252/186; 206/46 CC, 47 R, 47 A, 84; 8/111

[56] References Cited

UNITED STATES PATENTS

| | | | |
|---|---|---|---|
| 2,283,350 | 5/1942 | Baum .................................. | 424/62 |
| 2,991,228 | 7/1961 | Lustig .................................. | 424/62 |
| 3,190,803 | 6/1965 | Vogt .................................... | 424/62 |
| 3,206,364 | 9/1965 | Purlee ................................. | 424/62 |
| 3,378,444 | 4/1968 | Swanson ............................. | 424/62 |
| 3,649,159 | 3/1972 | Cohen et al. ...................... | 424/62 X |

FOREIGN PATENTS OR APPLICATIONS

| | | | |
|---|---|---|---|
| 940,799 | 6/1948 | France ............................... | 424/62 |
| 1,255,863 | 12/1967 | Germany ........................... | 424/72 |
| 78,053 | 4/1955 | Netherlands ....................... | 424/62 |
| 466,172 | 5/1937 | United Kingdom ................ | 424/62 |
| 859,276 | 1/1961 | United Kingdom ................ | 424/62 |
| 1,033,737 | 6/1966 | United Kingdom ................ | 424/177 |

*Primary Examiner*—V. D. Turner
*Assistant Examiner*—Vera C. Clarke
*Attorney, Agent, or Firm*—Charles R. Wilson; Richard C. Witte; Jack D. Schaeffer

[57] ABSTRACT

Hair bleaching compositions containing arginine or various proteins or polypeptides having a high arginine content, a peroxide compound and a bleaching accelerator as essential components.

5 Claims, No Drawings

HAIR BLEACHING COMPOSITIONS CONTAINING AN ARGININE COMPOUND

This is a continuation of application Ser. No. 129,554, filed Mar. 30, 1971, now abandoned.

BACKGROUND OF THE INVENTION

This invention relates to hair bleaching compositions containing arginine, or proteins or polypeptides having a high arginine content as the characterizing ingredient.

Bleaching compositions used on hair differ from those used with textiles, fabrics, in hard surface cleansing and the like in that hair bleaching compositions, in addition to oxidizing and destroying the colored melanin of the hair, must be suitable for use in contact with the human skin and must not damage the hair excessively. Furthermore, since hair bleaches are a member of the class of materials known as cosmetics it is desirable that they be aesthetically acceptable to the user. Finally, it is desirable that a hair bleaching composition remove the melanin coloration from the hair as quickly as possible, both for the sake of convenience and to help prevent untoward damage to the hair and irritation to the skin and scalp.

Hair bleaches commonly consist of a peroxide oxidizing agent, a bleaching accelerator, and a variety of additional cosmetic and bleach stabilizing agents. Oxidizing agents such as the various hypochlorites and halogenated cyanuric acid compounds suitable for use in hard surface and fabric bleaching are not suitable for use on hair since they are too damaging and too irritating to the skin. A disadvantage to the use of peroxide bleaches on hair is that they must be used at a basic pH. The most common material for adjusting the pH of peroxide hair bleaching compositions is an aqueous solution of ammonia, commonly referred to as ammonium hydroxide. Ammonium hydroxide, while widely used in commercial bleaches, suffers from at least two major disadvantages, to wit, it is irritating to the skin and it has a disagreeable odor which cannot be masked by perfume.

Since peroxide hair bleaches have to be used at basic pH's and because of the aforementioned disadvantages to the use of ammonium hydroxide for this purpose, a variety of other bases have been suggested for use in hair bleaching compositions. U.S. Pat. No. 2,283,350, granted May 19, 1942, to N. Baum, discloses the use of aliphatic amines and hydroxyaliphatic amines as substitutes for ammonium hydroxide in hair bleaching compositions. Moreover, the concurrently filed application of Knohl and Zeffren, entitled "Hair Bleaching Compositions and Process", filed Mar. 30, 1971. Ser. No. 129,555, now abandoned, relates to hair bleaches containing various guanidine compounds.

As will be described more fully hereinafter, hair bleaching compositions containing arginine or a protein having a high arginine content as an essential ingredient eliminate the problems associated with the use ammonium hydroxide in hair bleaching compositions in that said compositions have essentially no inherent odor and do not irritate the skin. Furthermore, the bleaching process inevitably causes some damage to the hair and this damage is usually attributed to the oxidation of cystine bonds in the hair polymer. This cystine oxidation damage is increased by higher peroxide concentrations in the bleach and by longer contact times of said bleach with the hair. In addition to the aforementioned benefits ascribable to the hair bleaching compositions of this invention, the presence of the arginine materials in said compositions quite unexpectedly permits the use of lower concentrations of peroxide and shorter bleaching times than do the prior art hair bleaches and thereby cause less hair damage. An added benefit is that the proteins and polypeptides used herein adsorb on the hair and improve its after-bleach appearance and condition.

Accordingly, it is an object of this invention to provide bleaching compositions which do not have an ammonia or amine odor and which are especially suited for use on growing hair. It is a further object to provide hair bleaching compositions which are faster acting and less damaging than prior art bleaches. It is still a further object to provide improved peroxide hair bleaching compositions containing arginine or certain proteins or polypeptides of the type hereinafter disclosed having a high arginine content. These and other objects are obtained by the present invention as will become apparent from the following disclosure.

SUMMARY OF THE INVENTION

The bleach compositions of this invention comprise: (1) from about 0.1 to about 20% by weight of a compound selected from the group consisting of arginine and protamine proteins and polypeptides containing a major proportion (50% by weight and greater) of arginine units in their structure, and the peroxide-compatible salts thereof; (2) from about 1 to about 10% by weight of a water-soluble peroxide compound; and (3) from about 1 of about 10% by weight of a water-soluble hair bleaching accelerator, said composition having a pH of from about 8 to about 11 in aqueous solution.

In addition, this invention encompasses a process for bleaching hair, especially growing human hair, comprising contacting said hair with a composition comprising peroxide, arginine or a protein or polypeptide having a high arginine content, or the peroxide-compatible salts thereof, and a bleaching accelerator while maintaining the pH of said composition in the range of about 8 to about 11.

DETAILED DESCRIPTION OF THE INVENTION

The bleaching compositions of this invention are maintained at an optimum pH of from about 8 to about 11, more preferably about 9 to about 10 when applied to the hair. Surprisingly, although this pH is in the normal range of hair bleaching compositions, an increase in the rate of hair bleaching is noted with the present compositions. While not intending to be restricted by theory, it is hypothesized that the high arginine content of the compositions enhances the penetration of the peroxide into the hair shaft, thereby increasing the rate of melanin bleaching. Whatever the reason for the improved hair bleaching activity of the present compositions, the improvement is not attributable merely to the pH, but is related to the presence of the arginine or protamine proteins.

The amino acid, arginine, or its peroxide-compatible salts, as hereinafter detailed, is one essential component of the bleaching compositions of this invention. Alternatively, proteins or polypeptides having a high arginine content can be used herein in place of arginine to provide the enhanced bleaching activity. The pure amino acid, the protein, the polypeptides containing a major proportion of arginine units, and their respective salts are referred to collectively herein as "arginine compounds." Proteins having a major proportion of arginine units in their structures are members of that class of proteins known as protamines. While it is not possible to specify with certainty the complete structures of each member of this class since few of their amino acid sequences have been determined, the protamine proteins all have several common characteristics. The most distinctive features of this class of proteins are: (a) a low molecular weight, in the range of about 5,000; (b) a high isoelectric point, in the pH range of about 10 to 12; and (c) a high arginine content, in the range from about 50 to about 90%, by weight, of the total protein. Protamine proteins having a high arginine content suitable for use herein are listed in R. J. Block and K. W. Weiss, "Amino Acid Handbook", Thomas, Springfield, Ill. (1956), page 260, et seq. Some of the protamine proteins of high arginine content suitable for use herein include: clupein, obtainable from herring; fontinin, obtainable from salmon; salmin, obtainable from salmon, iridin, obtainable from rainbow trout, lacustrin, obtainable from sea trout, gallin, obtainable from fowl; sturin, obtainable from sturgeon; sperm nucleoprotein from mollusks (Patella coerulea); and macerated bovine testes. All of the above proteins of the protamine class have an arginine content greater than 50% and are suitably employed herein.

Proteins of the type hereinabove described can be subjected to acid or base hydrolysis to yield polypeptides which also have a high arginine content. Such polypeptides are obtained, for example, during the processing of fish and fowl and can be employed in the bleaching compositions of this invention. Again, the exact chemical structure of these polypeptides cannot be specified with certainty in that they have very complex amino acid sequences. As in the case of their parent proteins, which are protamines of the type hereinabove disclosed, the polypeptides useful herein have a molecular weight below about 5,000, are basic (pH 10–12), and have an arginine content of about 50%, or greater, by weight.

Since arginine and the protamine proteins and polypeptides having an arginine content of 50%, or greater, are basic, they are often isolated from natural sources in the form of salts. Such salts are suitable for use herein, if their anions are compatible with peroxides, especially hydrogen peroxide. Arginine salts, protamine protein salts and protamine polypeptide salts are formed by reacting these materials with mineral acids such as hydrochloric acid, phosphoric acid, carbonic acid, sulfuric acid, nitric acid, etc., and the organic acids such as formic acid, acetic acid, lauric acid, chloroacetic acid and the like, each of which provide anions which are compatible with peroxides. Acids containing metallo-anions and strongly reducing anions, e.g., chromic acid and hydrogen thiocyanate, are not suitable herein in that these anions react with the peroxide.

Reaction of the aforementioned proteins, etc., with the exemplary acids yields exemplary salts useful herein. For example, arginine chloride, arginine carbonate, arginine sulfate, salmin sulfate, clupein hydrochloride, iridin phosphate, lacustrin carbonate, gallin carbonate, sturin chloride, sperm nucleoprotein hydrochloride, arginine phosphate, acid hydrolyzed sturin pyrophosphate, arginine nitrate, base hydrolyzed gallin acetate, hydrolyzed lacustrin chloroacetate, and the like are suitable for use in the compositions of this invention.

The arginine, protamine protein, protamine polypeptides, and peroxide compatible salts thereof, are used herein at concentrations from about 0.1 to 20%, preferably 0.5 to about 9% by weight of the total bleach composition. The phosphates and carbonate salts are preferred for this purpose in that they are self-buffering. Arginine phosphate, arginine carbonate, arginine and arginine chloride are especially preferred for use herein. Clupein carbonate and salmin phosphate are likewise preferred.

The peroxide component of the present compositions is preferably hydrogen peroxide or any of the water-soluble alkali metal peroxides, e.g., sodium and potassium peroxide, etc. Alkaline earth metal peroxides, organic peroxides and the peroxide complexes such as the water-soluble addition compounds of materials such as urea and guanidine with hydrogen peroxide are suitable herein. Examples of some of these materials include urea peroxide (preferred), guanidine peroxide, and the like. Preferred compounds having the elements of hydrogen peroxide in their structures also include sodium perborate. The peroxide component of the bleaches described herein usually comprises from about 1 to about 10% by weight of the total composition. A peroxide concentration of about 2 to 6% by weight is preferred for use in the hair bleaching compositions of this invention.

The peroxide bleaching compositions herein contain additional agents to improve performance; there are referred to herein as bleaching accelerators. The bleaching compositions disclosed herein can employ any of the well-known hair bleaching accelerating agents such as ammonium peroxydisulfate or alkali metal peroxydisulfates or any of the other common peroxygen salts commonly used in hair bleaching compositions such as the ammonium or alkali metal peroxydiphosphates described in South African Patent No. 692,638, published Nov. 26, 1969, to B. Cohen. Mixtures of any of the foregoing bleaching accelerators are also suitable. Such bleaching accelerators are used at a concentration from about 1 to about 10%, preferably 3 to 8% by weight. Ammonium peroxydisulfate, the potassium and sodium peroxydisulfates and potassium peroxydiphosphate are preferred bleach accelerators for use herein.

As noted hereinabove, peroxide containing hair bleaches are used in the basic pH range and bases such as the alkali metal hydroxides, ethanolamine, and the like can be used to adjust the pH. During the course of the hair bleaching operation the pH of the bleach composition will sometimes change; therefore, in a preferred embodiment of this invention a buffer is included in the composition to maintain a relatively constant pH within the desired range. Any of the common peroxide-stable buffers suitable for use in the pH range from 8 to 11 can be used herein for this purpose, e.g., carbonates, $Na_2HPO_4$, $NaH_2PO_4$, etc. Especially preferred herein are phosphate buffers, especially ortho-, meta-, tri-polyphosphate salts. While any of the common buffers are useful herein, the phosphate buffer salts have the advantage that they are innocuous when applied to the skin, are efficient buffers over the pH range indicated, and stabilize the peroxide being used by preventing metal ion catalyzed peroxide decomposition. Buffers such as the phosphates can be used at concentrations from about 0.1 to about 5% by weight in the present compositions. When the phosphate and carbonate salts or arginine and the protamine proteins are used herein they act as their own pH buffers and maintain the basicity of the bleaching composition within the optimal range. When such phosphate or carbonate salts are used herein some additional base or buffer can be included to help maintain pH stability and to help stabilize the peroxide.

Hair bleaching compositions designed for use on the head are difficult to apply properly without the use of thickeners. It is therefore desirable to include thickening agents in the herein disclosed compositions to impart a creamy gel consistency thereto such that they are adapted for localized application. A variety of such thickening agents suitable for use with peroxide hair bleaching compositions are well-known in the cosmetic arts and all such thickeners are useful in the present compositions. For example, sodium metasilicate is commonly used for this purpose as are various clays, carboxymethylcellulose compounds and the like. Thickeners can be used at concentrations from about 1 to about 5% of the bleaching compositions.

The present compositions can contain various other adducts to provide a more cosmetically acceptable product. Such materials as perfumes, dyes, and the like can be added to the bleaching compositions detailed herein to provide a more pleasant cosmetic aspect.

The compositions of this invention can be provided in kit form as separately packaged components to maintain stability, and mixed by the user immediately prior to application to the hair. The peroxide compound, e.g., hydrogen peroxide, at about 1 to 30% by weight aqueous solution, comprises one of the individually packaged components of such bleach compositions. The separately packaged peroxide component can contain trace quantities of stabilizers such as the ethylenediaminetetraacetates, phosphates, citrate and the like. The second component comprises the arginine, protamine protein or polypeptide, or salts thereof, and the bleaching accelerator, along with any auxiliary agents such as the aforementioned pH buffers, peroxide stabilizers, perfumes, thickening agents, and the like. In the case of the dry bleach compositions hereinafter detailed, the peroxide, arginine, protamine protein or polypeptides, or salts thereof, bleach accelerator, buffer salts, etc., are packaged together and are added to water, or the liquids noted below, prior to use.

The following examples serve to illustrate the bleaching compositions of this invention but are not intended to be limiting thereof. In the examples, water is used as the common vehicle for the components of the bleach compositions. Water can be replaced, wholly or in part, by liquids such as the lower alcohols, e.g., ethanol, isopropyl alcohol, ethylene glycol, glycerine and mixtures thereof. While the peroxide sources used herein are all water-soluble, the arginine proteins and salts thereof can be present as colloidal suspensions or emulsions. The bleaches herein are applied to hair for periods from one minute to 4 hours, depending on the degree of bleaching desired.

EXAMPLE I

| Ingredient | Amount |
| --- | --- |
| Arginine hydrochloride | 4.5 g. |
| Sodium tripolyphosphate | 2.0 g. |
| Ammonium peroxydisulfate | 3.0 g. |
| Hydrogen peroxide (30% wt. solution) | 5.0 g. |
| Water | & To 50 ml. |
| | Total Volume |

The arginine hydrochloride, sodium tripolyphosphate and ammonium peroxydisulfate are dissolved in about 30 ml. of water, the hydrogen peroxide is added and the resulting solution is diluted to 50 ml. The final concentration (wt.) of the bleaching solution of this composition is 3% hydrogen peroxide, 6% ammonium peroxydisulfate, 9% arginine hydrochloride and 4% sodium tripolyphosphate; the pH is 9. This odorless bleaching solution is applied to hair and rapidly bleaches it with minimal damage.

EXAMPLE II

| Ingredient | Amount |
| --- | --- |
| Arginine carbonate | 4.5 g. |
| Ammonium peroxydisulfate | 3.0 g. |
| Hydrogen peroxide (30% by weight aqueous solution) | 5.0 g. |
| Water | & To 50 ml. |
| | Total Volume |

The above bleaching composition is prepared by dissolving the arginine carbonate and the ammonium peroxydisulfate in about 30 ml. of water, adding the hydrogen peroxide and diluting the resulting solution to 50 ml. The final concentration in this bleach is 3% hydrogen peroxide, 6% ammonium peroxydisulfate and 9% arginine carbonate; the pH is 9.2. The odorless self-buffering bleaching composition prepared in this manner is applied to human hair and rapidly bleaches it.

EXAMPLE III

| Ingredient | Amount |
| --- | --- |
| Clupein | 0.05 g. |
| Sodium tripolyphosphate (STP) | 1.5 g. |
| Potassium peroxydisulfate | 3.0 g. |
| Hydrogen peroxide (30% by weight aqueous solution) | 5.0 g. |
| Water | & To 50 ml. |
| | Total Volume |

The above bleaching composition is prepared by mixing the clupein, the STP and the potassium peroxydisulfate in about 30 ml. of water, adding the hydrogen peroxide and diluting the resulting mixture to 50 ml. The final concentration in this bleach is 3% hydrogen peroxide, 6% potassium peroxydisulfate, 0.1% clupein and 3% STP; the pH is 9.2. This odorless bleaching composition is applied and rapidly bleaches human hair and leaves a cosmetically beneficial protein film thereon.

In the above composition the clupein is replaced by an equivalent amount of sturin, iridin, salmin, lacustrin, gallin, base hydrolyzed clupein, acid hydrolyzed iridin, iridin carbonate, clupein carbonate, fontinin, gallin phosphate, sperm nucleoprotein and macerated bovine testes, respectively, and equivalent odorless bleaching compositions are thereby secured. The respective bleaches are applied to hair for periods from about 10 minutes to 4 hours, depending on the degree of lightening desired, and effectively bleach the hair and deposit a cosmetic coating thereon.

EXAMPLE IV

Thickened Bleaching Composition

| Ingredient | Percent (wt.) |
| --- | --- |
| Arginine carbonate | 9% |
| Ammonium peroxydisulfate | 1% |
| Hydrogen peroxide (30% by weight aqueous solution) | 8% |
| Sodium metasilicate | 2% |
| Water | Balance |

The above bleaching composition is prepared by dissolving the arginine carbonate, the ammonium peroxydisulfate and the hydrogen peroxide in about 50 ml. of water and adding the sodium metasilicate to provide a thickened solution. Bleaching compositions so obtained are essentially odorless and rapidly bleach growing human hair.

In the above composition the arginine carbonate is replaced by an equivalent amount of clupein phosphate, salmin phosphate, iridin bicarbonate, clupein acetate, and sperm nucleoprotein laurate, respectively. The equivalent hair bleaching compositions so obtained rapidly and safely bleach human hair. The pH is adjusted to 8.0 with HCl and equivalent bleaches are secured.

In the above composition the ammonium peroxydisulfate is replaced by an equivalent amount of sodium peroxydisulfate, potassium peroxydiphosphate, and potassium peroxydisulfate, respectively, and equivalent bleaching results are secured.

EXAMPLE V

Dry Peroxide Bleaching Composition

| Ingredient | Percent (wt.) |
| --- | --- |
| Iridin | 20% |
| Sodium perborate | 5% |
| Potassium peroxydisulfate | 8% |
| Ammonium peroxydisulfate | 2% |
| Sodium metasilicate | 2% |
| Sodium tripolyphosphate | 2% |
| Starch | Balance |

The above composition is mixed with 50 ml. of water and adjusted to pH 11 with ethanolamine and provides a thickened, buffered bleaching composition which rapidly and safely bleaches hair. The composition is essentially odorless.

In the above composition, each of the following modifications are made:

The sodium perborate is replaced by an equivalent amount of potassium peroxide, peroxyacetic acid, peroxybenzoic acid, p-chloroperoxybenzoic acid, and ethylperoxyacetic acid, respectively, and the resulting bleach compositions thereby secured are applied to human hair for periods from about 10 minutes to about 2 hours, depending upon the degree of lightness desired, and effectively bleach said hair.

The potassium peroxydisulfate is replaced by an equivalent amount of a 1:1 (wt.) mixture of ammonium peroxydisulfate and ammonium peroxydiphosphate and equivalent bleaching compositions are secured.

The potassium metasilicate is replaced by an equivalent amount of sodium carboxymethylcellulose and a thickened bleach is thereby secured.

The sodium tripolyphosphate is replaced by an equivalent amount of sodium hydrogen phosphate, sodium dihydrogen phosphate and a mixture (1:1 wt.) of sodium hydrogen phosphate and sodium citrate and buffered bleaches are secured.

The sodium perborate is replaced by sodium peroxide at concentrations of 1 and 10%, by weight, respectively, and hair bleaching compositions are thereby provided. The sodium perborate in the above compositions is replaced by urea peroxide at concentrations of 1 and 10%, by weight, respectively, and odorless hair bleaches are thereby secured.

Hair bleaching products are typically marketed in kit form, i.e., a package comprising an individually packaged oxidizing component and an individually packaged bleaching assistant. In an embodiment of this invention said oxidizing component consists of an aqueous solution of a peroxide as detailed herein, most generally aqueous hydrogen peroxide having a concentration from about 1 to about 10% by weight, and said bleaching assistant component comprises a bleaching accelerator of the type hereinbefore detailed and an arginine or protamine compound or salt thereof, of the type hereinabove detailed. The components are mixed by the user immediately prior to application to the hair. An example of such kit is as follows:

A hair bleaching kit is assembled comprising a single package including therein: (1) a 4 oz. bottle of hydrogen peroxide (6% by weight $H_2O_2$); and (2) a foil packet containing a bleaching assistant, said assistant consisting of 4 g. of ammonium peroxydisulfate, 4 g. of arginine carbonate, 2 g. of sodium carboxymethylcellulose and 20 g. of starch. The bleaching assistant is admixed with the hydrogen peroxide and the solution is applied to the hair and bleaches it.

In the above composition the arginine carbonate is replaced by an equivalent amount of arginine phosphate, clupein carbonate, clupein phosphate, salmin carbonate and salmin phosphate, respectively, and equivalent results are secured.

In the above composition the 6% aqueous hydrogen peroxide solution is replaced by an equivalent volume of 3% hydrogen peroxide solution and equivalent results are secured.

In the above composition the arginine carbonate is replaced by an equivalent amount of arginine, clupein, fontinin, salmin, iridin, lacustrin, gallin, sturin, sperm nucleoprotein and macerated bovine testes, respectively, and 5 g. of a buffer consisting of 4 g. of $Na_2HPO_4$ and 1 g. of $NaH_2PO_4$ is included in the bleaching assistant packet. Upon admixture with the peroxide, buffered (pH 9.2) bleaches are secured.

What is claimed is:

1. A hair bleaching composition comprising: (1) from about 0.1 to about 20% by weight of an arginine compound selected from the group consisting of arginine, arginine carbonate, arginine chloride, and arginine phosphate; (2) from about 1 to about 10% by weight of a water-soluble peroxide compound; and (3) from about 1 to about 10% by weight of a water-soluble hair bleaching accelerator selected from the group consisting of ammonium peroxydisulfate, alkali metal peroxydisulfate, ammonium peroxydiphosphate, alkali metal peroxydiphosphate, and mixtures thereof, said composition having a pH of from about 8 to about 11 in aqueous solution.

2. A composition according to claim 1 wherein the water-soluble peroxide compound is selected from the group consisting of hydrogen peroxide, alkali metal peroxides, sodium perborate, and urea peroxide.

3. A composition according to claim 2 wherein the bleaching accelerator is selected from the group consisting of ammonium peroxidisulfate, potassium peroxydisulfate, sodium peroxydisulfate, potassium peroxydiphosphate, and mixtures thereof.

4. A composition according to claim 3 containing from about 0.5 to about 9% by weight of the arginine compound.

5. A composition according to claim 4 containing from about 2 to about 6% by weight of the water-soluble peroxide compound.

* * * * *